United States Patent [19]

Pelter et al.

[11] 4,271,317
[45] Jun. 2, 1981

[54] ALKYLBORANE COMPLEXES

[75] Inventors: Andrew Pelter, Swansea, Wales; David J. Ryder, Chesham, England

[73] Assignee: Imperial Chemical Industries Limited, London, England

[21] Appl. No.: 90,085

[22] Filed: Oct. 31, 1979

[30] Foreign Application Priority Data

Nov. 7, 1978 [GB] United Kingdom ............... 44265/78

[51] Int. Cl.$^3$ ............................................. C07C 87/28
[52] U.S. Cl. ................... 564/8; 260/313.1; 544/106; 548/110; 568/715; 568/716; 568/814; 568/846; 568/837
[58] Field of Search ............... 260/583 A, 576, 313.1; 544/106; 548/110

[56] References Cited

U.S. PATENT DOCUMENTS 3,257,455  6/1966  Ashby ............................ 260/583 A

OTHER PUBLICATIONS

Pelter et al., Tetrahedron Letters No. 47, 4715-4718 (1978).
Brown et al., JACS 97 (10) 2791-2798 (1975).
Negishi et al., Synthesis pp. 77-89 (1974).
Lane, Aldrichimica Acta 6 pp. 51-58 (1973).
Ashby, JACS 81 pp. 4791-4795 (1959).

Primary Examiner—Helen M. S. Sneed
Attorney, Agent, or Firm—Cushman, Darby & Cushman

[57] ABSTRACT

The invention relates to alkylborane complexes with aromatic amines of the formula:

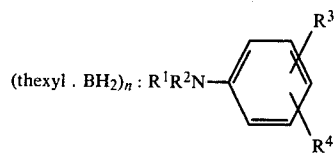

in which $R^1$ and $R^2$ are the same or different (1-4C)-alkyl radicals, or together with the adjacent nitrogen atom are morpholino, piperidino or pyrrolidino radicals; $R^3$ and $R^4$ are independently selected from hydrogen, (1-4C)-alkyl, (1-4C)-alkoxy, di-(1-4C)-alkylamino, morpholino, piperidino and pyrrolidino; thexyl stands for 1,1,2-trimethylpropyl; and n is the integer 1 when $R^3$ and $R^4$ are other than nitrogen containing radicals, or the integer 1 or 2 when one of $R^3$ and $R^4$ is a nitrogen containing radical, or the integer 1, 2 or 3 when both $R^3$ and $R^4$ are nitrogen containing radicals.

The complexes are more stable than thexylborane tetrahydrofuran complex, but are sufficiently reactive to be valuable as hydroborating and reducing agents.

The invention also provides solutions of the complexes of formula I in organic solvents for convenient storage or subsequent synthetic use, and a process for manufacturing said complexes.

A particularly convenient complex of the invention is thexylborane N,N-diethylaniline complex.

9 Claims, No Drawings

ALKYLBORANE COMPLEXES

This invention relates to complexes of alkyl boranes with aromatic amines and in particular it relates to complexes of thexylborane with aromatic amines which are of value in general synthetic organic chemistry as hydroborating and reducing agents.

The complex of 1,1,2-trimethylpropylborane (also known as thexylborane) with tetrahydrofuran (THF) is a bifunctional hydroborating agent that has found many applications in reactions involving two migrations from boron to carbon. However the complex undergoes isomerisation (E. Negishi and H C Brown, *Synthesis,* 1974, 77) and must be made in the cold immediately before use. A more stable complex of thexylborane with triethylamine is also known, but hydroboration of alkenes with this complex is accompanied by production of a monoalkylborane triethylamine complex with displacement of 2,3-dimethylbut-2-ene(thexene) (H C Brown et alia, *J. Organometallic Chemistry* 1977, 135, C10).

Amine complexes of borane itself are also known but have found little place as synthetic reagents because of their low activity as hydroborating and reducing agents (C F Lane, "The Borane-Amine Complexes", *Aldrichimica Acta,* 1973, 6, 51; and R Koster, *Angew Chem.* 1957, 69, 684). Thus, borane-triethylamine complex only hydroborates hex-2-ene at 200° C. at which temperature isomerisation occurs so that the sole product is tri-n-hexylborane. Addition of Lewis acids to remove the amine by preferential complexation has met with only limited success. Thus, the hydroboration of oct-1-ene with borane-pyridine complex in the presence of boron trifluoride ethereate required 16 hours at 75° C. (E C Ashby, *J.Am.Chem.Soc.* 1959, 81, 4791).

We have now discovered a novel group of complexes of thexylborane with aromatic amines, which are both stable and yet undergo ready hydroboration of alkenes and are active reducing agents.

According to the invention there is therefore provided a complex of the formula:

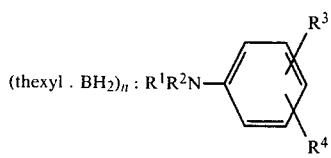

wherein $R^1$ and $R^2$ are the same or different (1-4C)-alkyl radicals, or together with the adjacent nitrogen constitute a morpholino, piperidino or pyrrolidino radical; $R^3$ and $R^4$ are independently selected from hydrogen, (1-4C)-alkyl, (1-4C)-alkoxy, di-(1-4C)-alkylamino, morpholino, piperidino and pyrrolidino radicals; thexyl is a 1,1,2-trimethylpropyl radical; and n is the integer 1, when $R^3$ and $R^4$ are other than nitrogen containing radicals, or the integer 1 or 2 when one of $R^3$ and $R^4$ is a nitrogen containing radical, or the integer 1, 2 or 3 when both $R^3$ and $R^4$ are nitrogen containing radicals.

It is to be understood that in the specification the term "complex" includes both a formal complex and a relatively loose physical association containing stoichiometric amounts of amine and thexylborane.

A particular value for $R^1$ and $R^2$ when they are (1-4C)-alkykl radicals is, for example, methyl or ethyl radicals, and a particularly suitable value for the radical $R^1R^2N$ is, for example, a dimethylamino or diethylamino radical.

A particular value for $R^3$ or $R^4$, when either is a (1-4C)-alkyl or (1-4C)-alkoxy radical is, for example, a methyl or methoxy radical, and when either is a di-(1-4C)-alkyl radical is, for example, a dimethylamino or diethylamino radical.

When $R^3$ or $R^4$ are nitrogen containing radicals it is preferred that they have the same value as the radical of the formula $NR^1R^2$. When one of $R^3$ and $R^4$ is a nitrogen containing radical it is preferably located in the para position relative to the radical $NR^1R^2$. When both $R^3$ and $R^4$ are nitrogen containing radicals they are preferably located in the meta positions relative to the radical $NR^1R^2$.

In a preferred mode of the invention n is the integer 1, $R^3$ is hydrogen and $R^4$ is selected from hydrogen, 4-methyl and 4-methoxy radicals.

Particular complexes of formula I which are of special interest are, for example, those between thexylborane and N,N-dimethylaniline, N,N-diethylaniline, N-phenyl-morpholine, N-phenylpiperidine or N-phenylpyrrolidine, of which that between thexylborane and N,N-diethylaniline is especially preferred, and will be referred to hereinafter as TBDA.

The complexes may be made by conventional procedures, which are provided as a further feature of the invention. Thus they may be made by generating one or more molecular equivalents of thexylborane in a suitable dry solvent, for example a complexing solvent such as tetrahydrofuran, for example under the conditions described by E Negishi and H C Brown (*Synthesis,* 1974, 77), and then adding one molecular equivalent of an aromatic amine of the formula:

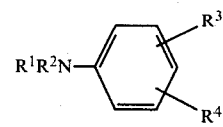

wherein $R^1$, $R^2$, $R^3$ and $R^4$ have the meanings defined above, preferably at a temperature of, for example, −20° to 5° C.

It will be recognised that the amount of thexylborane used is dependent on the number of nitrogen containing radicals in the amine of formula II, and on the value of n required. In general, however, it is preferred that one additional molecular equivalent of thexylborane is used for each additional nitrogen containing radical that is present. The original solvents including any complexing solvents such as tetrahydrofuran may be removed by evaporation so that the complex of formula I may be obtained per se and used neat or redissolved in another suitable solvent.

Suitable solvents are, for example, non-complexing solvents such as petroleum ether fractions, hexane, benzene, toluene or xylene or complexing solvents such as diethyl ether, 1,2-dimethoxyethane, tetrahydrofuran or diethylene glycol dimethyl ether. A solution of a complex of formula I in such a solvent is a convenient form in which to use or store a complex of formula I and is provided as a further feature of the invention.

The complexes of formula I are in general stable for long periods, either alone or in solution, for example in tetrahydrofuran. Thus, a solution of TBDA in tetrahydrofuran showed no isomerisation or loss of hydride activity when stored at 0° C. for a period of two months.

The preparation and synthetic utility of the complexes of the invention will now be illustrated in the following non-limiting Examples:

EXAMPLE 1

A solution of thexylborane in tetrahydrofuran was obtained from diborane and tetramethylethylene using the same conditions and quantities as those of H C Brown et alia in *J. Org. Chem.* 1972, 37, 2949. N,N-Diethylaniline (1 molar equivalent) was then added to the thexylborane solution and the mixture evaporated in vacuo to give thexylborane diethylaniline complex (TBDA) as a viscous syrup in essentially quantitative yield, having the following infra-red spectral absorption maxima:

| Sample | Band I cm$^{-1}$ | Band II cm$^{-1}$ |
|---|---|---|
| liquid film | 1572 | 2513 |
| 6.8% w/v soln. in tetrahydrofuran | 1578 | 2513 |
| 6.4% w/v soln. in benzene | 1574 | 2513 |
| 8.0% w/v soln. in cyclohexane | 1574 | 2512 |

Nuclear magnetic resonance (NMR) spectral examination of a solution of the complex in deuterobenzene compared with boron trifluoride trietherate as a standard in separate coaxial cells at 30.08 MHz and with H$^1$ decoupled indicated the complex to possess a B$^{11}$ signal with chemical shift of 777.01 Hz (relative to BF$_3$.Et$_2$O). By way of comparison, the known complex of thexylborane with triethylamine (TBTA) showed a B$^{11}$ signal with chemical shift of 777.63 Hz and thexylborane dimer a B$^{11}$ signal with chemical shift of 775.20 Hz.

The thexylborane diethylaniline complex is easily soluble in hexane, benzene, diethyl ether, 1,2-dimethoxyethane and tetrahydrofuran and is conveniently used in solution in any of such solvents for subsequent synthetic use, for example for hydroboration or reduction reactions.

EXAMPLE 2

Using a similar procedure to that described in Example 1, but replacing N,N-diethylaniline by N-phenylmorpholine, thexylborane N-phenylmorpholine complex may be obtained as a viscous syrup having a satisfactory nuclear magnetic resonance spectrum and infrared spectrum.

EXAMPLE 3

A solution of TBDA in tetrahydrofuran was reacted with one molar equivalent of cyclohexene at 0° C. for 2 hours to give the hydroboration adduct (thexyl) (cyclohexyl) borane as its diethylaniline complex. Addition of one molar equivalent of oct-1-ene to this solution at 0° C. gave (thexyl) (octyl) (cyclohexyl)borane as its diethylaniline complex. At no stage was thexene produced. This solution was then reacted using a similar procedure to that of Pelter et alia (*Chemical Communications,* 1970, 1529-1530) with a 0.2 molar excess of powdered sodium or potassium cyanide. Thus the cyanide was added at 0° C. and the mixture then stirred without cooling at room temperature for 45 minutes. The mixture was then cooled to −78° C. and treated with trifluoroacetic anhydride (0.5 molar excess), and then allowed to warm up to room temperature during 1-2 hours. The mixture was then oxidised, first at room temperature for 3 hours and then at 50° C. for 1 hour, with an excess of aqueous sodium peroxide solution. The mixture was then diluted with water and extracted with pentane. Evaporation of the extracts gave cyclohexyl n-octyl ketone, identical with authentic material, in 78% yield.

EXAMPLE 4

This example compares the reactivity of TBDA with thexylborane-tetrahydrofuran using the same conditions as those described by H C Brown et alia *J.Org.-Chem.* 1972, 37, 2942. Thus, 2.5 m mole of substrate was reacted with 5 m mole of TBDA in sufficient tetrahydrofuran to give 10 ml. of solution, 1.0 M in hydride. Aliquots were withdrawn periodically for hydride analysis and products were identified by g.l.c. and spectroscopic comparison with authentic materials.

(1) Alcohols and thiols

TBDA in general reacts faster than thexylboranetetrahydrofuran (THF), as summarised below:

| | Thexylborane-THF* | | TBDA | |
|---|---|---|---|---|
| Substrate | Hydride used | Time | Hydride used+ | Time |
| Benzyl alcohol | 1.00 | 0.5 hr | 1.00 | 3.5 min |
| Phenol | 1.00 | 6 hr | 1.00 | 6 min |
| C$_6$H$_{13}$SH | 1.00 | 10 hr | — | — |
| EtSH | — | — | 1.00 | 3 hr |
| Thiophenol | 0.92 | 24 hr | 1.00 | 0.5 hr |

*J.Org.Chem. 1972, 37, 2942
+All hydride was used in evolution of hydrogen, not in reduction.

(ii) Aldehydes and Ketones

The reduction of aldehydes and ketones with TBDA to the corresponding alcohol proceeds at rates comparable to those of thexylborane-THF. Cinnamaldehyde may be completely reduced by excess TBDA, but treatment with 1 molar equivalent at 0° C. for 15 minutes produces cinnamyl alcohol (70% yield) as the sole product. Similarly, only the aldehyde group of campholenic aldehyde is reduced to give the corresponding alcohol in 80% isolated yield.

(iii) Carboxylic acids

Extended reflux of carboxylic acids with excess thexylborane-THF is known to give aldehydes. By contrast TBDA at 0° C. reduces aliphatic carboxylic acids to give predominantly the corresponding alcohols. Benzoic acid in THF is only reduced to the extent of 15% in 48 hours whereas in benzene 1.98 equivalents of hydride are taken up in 2.5 hours. 10-Undecenoic acid reacts only at the double bond with one equivalent of TBDA at 0° C. in 15 minutes. Hydrolysis of the intermediate organoborane gives undecanoic acid in 90% isolated yield.

(iv) Tertiary amides

Aliphatic acid aromatic tertiary amides react with TBDA to give the corresponding tertiary amines at a rate at least ten times greater than with thexylborane-THF. Thus, N,N-dimethyl-benzamide and N,N-dimethylhexamide are reduced by 2 molar equivalents of TBDA in 3 and 6 hours respectively whereas reduction with 2 molar equivalents of thexylborane-THF needs 48 and 72 hours respectively.

EXAMPLE 5

This Example compares the reactivity of TBDA with thexylborane triethylamine complex (TBTA) prepared according to the procedure of H C Brown and N M Yoon (*J.Amer.Chem.Soc.* 1977, 99, 5514). Thus 2.5 m mole of substrate (benzaldehyde or pentan-3-one) was reacted with 5 m mole of TBDA or TBTA in sufficient tetrahydrofuran to give 10 ml. of solution containing 1.0 M hydride. Aliquots were withdrawn at intervals and the time for complete reaction to benzyl alchol or pentan-3-ol (confirmed by GLC comparison with authentic materials) was noted. The following results were obtained:

| Substrate | Reagent: time for complete reaction (hr.) | |
| --- | --- | --- |
|  | TBDA | TBTA |
| Benzaldehyde | <0.25 | 1.0 |
| Pentan-3-one | 0.25 | 3.0 |

What is claimed is:

1. A complex of the formula:

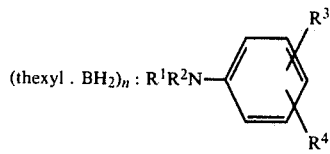   I wherein $R^1$ and $R^2$ are the same or different (1-4C)-alkyl radicals, or together with the adjacent nitrogen atom constitute a morpholino, piperidino or pyrrolidino radical; $R^3$ and $R^4$ are independently selected from hydrogen, (1-4C)-alkyl, (1-4C)-alkoxy, di-(1-4C)-alkylamino, morpholino, piperidino and pyrrolidino radicals; thexyl is a 1,1,2-trimethylpropyl radical; and n is the integer 1 when $R^3$ and $R^4$ are other than nitrogen containing radicals, or the integer 1 or 2 when one of $R^3$ and $R^4$ is a nitrogen containing radical, or the integer 1, 2 or 3 when both $R^3$ and $R^4$ are nitrogen containing radicals.

2. A complex as claimed in claim 1 wherein $R^1$ and $R^2$ are independently methyl or ethyl radicals, or together with the adjacent nitrogen atom constitute a morpholino, piperidino or pyrrolidino radical; and $R^3$ and $R^4$ are independently selected from hydrogen, methyl, methoxy, dimethylamino, diethylamino, morpholino, piperidino and pyrrolidino radicals.

3. A complex as claimed in claim 1 wherein $R^1$ and $R^2$ are both methyl or ethyl radicals, or together with the adjacent nitrogen atom constitute a morpholino, piperidino or pyrrolidino radical.

4. A complex as claimed in claim 1, wherein n is the integer 1.

5. A complex as claimed in claim 1, wherein n is the integer 1 and both $R^3$ and $R^4$ are other than nitrogen containing radicals.

6. A complex as claimed in claim 1 wherein n is the integer 1, $R^3$ is hydrogen and $R^4$ is selected from hydrogen, 4-methyl and 4-methoxy radicals.

7. The complex between thexylborane and N,N-diethylaniline.

8. The complex between thexylborane and N-phenylmorpholine.

9. A composition comprising a solution of a complex of formula I as claimed in claim 1 in a non-complexing or complexing solvent.

* * * * *